US008926576B2

(12) United States Patent
Mikkaichi (10) Patent No.: US 8,926,576 B2
(45) Date of Patent: Jan. 6, 2015

(54) MEDICAL DEVICE (71) Applicant: Olympus Medical Systems Corp., Tokyo (JP)

(72) Inventor: Takayasu Mikkaichi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/944,366

(22) Filed: Jul. 17, 2013

(65) Prior Publication Data
US 2014/0031773 A1 Jan. 30, 2014

Related U.S. Application Data (63) Continuation of application No. PCT/JP2012/080744, filed on Nov. 28, 2012.

(60) Provisional application No. 61/564,943, filed on Nov. 30, 2011.

(51) Int. Cl.
*A61M 1/00* (2006.01)
*A61B 17/11* (2006.01)
*A61M 27/00* (2006.01)

(52) U.S. Cl.
CPC .......... *A61M 1/0039* (2013.01); *A61B 17/1114* (2013.01); *A61M 27/00* (2013.01); *A61B 2217/005* (2013.01); *A61B 2217/007* (2013.01)
USPC ............................ 604/319; 604/540; 604/541

(58) Field of Classification Search
CPC .................................................. A61M 1/0039
USPC ............ 604/319, 313, 317, 540–543; 606/86, 606/190; 600/201, 206
See application file for complete search history.

(56) References Cited

U.S. PATENT DOCUMENTS 6,371,968 B1 * 4/2002 Kogasaka et al. ............. 606/190
7,520,872 B2 * 4/2009 Biggie et al. .................. 604/319

FOREIGN PATENT DOCUMENTS

| GB | 1 588 072 A | 4/1981 |
| JP | A-53-108694 | 9/1978 |
| JP | A-2006-505316 | 2/2006 |
| JP | A-2008-512181 | 4/2008 |
| JP | A-2009-066178 | 4/2009 |
| WO | WO 2004/041346 A1 | 5/2004 |
| WO | WO 2006/031410 A2 | 3/2006 |

OTHER PUBLICATIONS

Dec. 25, 2012 International Search Report issued in International Application No. PCT/JP2012/080744 (with translation).

* cited by examiner

*Primary Examiner* — Tatyana Zalukaeva
*Assistant Examiner* — Benedict L Hanrahan
(74) *Attorney, Agent, or Firm* — Oliff PLC (57) ABSTRACT A medical device includes a longitudinal axis member, a suction member that is provided at a distal end of the longitudinal axis member, has a contact surface capable of coming into close contact with an inner wall of a bursiform cavity when inserted into the bursiform cavity, and has a plurality of communication passages that are open to the contact surface and communicate with a lumen, a suction source provided at a proximal end of the longitudinal axis member so as to be connected to the lumen, and a closing member that is provided at an axial end of the suction member, comes into contact with the opening, and airtightly seals the opening.

9 Claims, 12 Drawing Sheets

MEDICAL DEVICE

The application claims priority to U.S. Provisional Application No. 61/564,943, filed on Nov. 30, 2011 and is a continuation application based on PCT International Application No. PCT/JP2012/080744, filed on Nov. 28, 2012, the contents of which are incorporated herein by reference.

BACKGROUND OF THE INVENTION

1. Field of the Invention

The present invention relates to a medical device and, more particularly, to a medical device that can be properly used for medical treatment in which negative pressure is locally applied in the body.

2. Description of Related Art

There are various types of inflammation which occur at bursiform cavities in a body. For example, in an anterior resection of the rectum, when a complication is caused, an anastomotic leak is caused and may be developed to abscess formation. The best way to treat such an abscess occurring in the body is not known, and surgical procedures such as drainage of fluid, anastomosis excision, fistula formation, etc. and conservative procedures such as administration of broad-spectrum antibiotics, restriction of food ingestion based on parenteral nutrition, etc. are conducted.

The inflammation of the bursiform cavities in the body may include, for instance, appendicitis. Appendicitis is often treated by excising the vermiform appendix. On the other hand, when appendicitis is suspected, there are cases in which the appendicitis can be treated without excising the vermiform appendix, and cases in which there is no actual appendicitis.

As one of the aforementioned methods of treating the abscess or the inflammation, a wound treatment based on negative pressure (negative pressure therapy) is known. The negative pressure therapy is disclosed in, for instance, Published Japanese Translation No. 2006-505316 of the PCT International Publication. According to a specific example of this therapy, a foam is positioned and disposed in a bursiform cavity (including an abscess) in the body of a patient using an introducer as a collecting means for collecting contents of the bursiform cavity. The foam is, for instance, an open-cell polyurethane ether foam. This foam is connected to a vacuum device via a flexible thin tube. The vacuum device is equipped with a collecting unit that collects an outflow such as a liquid forcibly discharged from the bursiform cavity and a negative-pressure source that maintains the cavity under negative pressure.

When the disposition of the foam is completed, the introducer is removed. Next, the negative pressure is applied to the foam. Since this negative pressure is uniformly applied to a wall of the cavity by the foam, the bursiform cavity is contracted. As a result, the outflow such as liquid or necrotic tissue which is present in the cavity is forcibly discharged from the cavity. This discharge is collected in the collecting unit via a tube. Thereby, the inflammation in the cavity is effectively treated. After the treatment is completed, the foam is removed.

In the case of the negative pressure therapy, it is necessary to seal the bursiform cavity. In the case of the technique set forth in Published Japanese Translation No. 2006-505316 of the PCT International Publication, a sealing is achieved by a shape of the cavity treated by the foam as a pressure distributor, a structure (e.g., an anus of a patient) of a passage of the body into which the introducer is pressed, or a certain adhesive drape used for vacuum adjunct treatment of the surface of the body.

SUMMARY OF THE INVENTION

According to a first aspect of the present invention, a medical device for endoscopically conducting negative pressure therapy on a bursiform cavity having an opening in a body includes a longitudinal axis member which has a lumen extending along a longitudinal axis so as to be capable of being inserted into the body, a suction member which is provided at a distal end of the longitudinal axis member so as to be capable of being inserted into the bursiform cavity, the suction member having a contact surface for coming into close contact with an inner wall of the bursiform cavity when inserted into the bursiform cavity, and the suction member having a plurality of communication passages that are open to the contact surface and communicate with the lumen; a suction source which is provided at a proximal end of the longitudinal axis member so as to be connected to the lumen, and the suction source suctioning the inner wall via the plurality of communication passages; and a closing member which is provided at an axial end of the suction member, the closing member coming into contact with the opening and airtightly sealing the opening.

According to a second aspect of the present invention, in the medical device according to the first aspect, the closing member may be curved toward the suction member in a concave shape.

According to a third aspect of the present invention, the medical device according to the first aspect may include a pusher for moving the closing member. The lumen may be connected with the suction member, and the closing member may be mounted on the longitudinal axis member so as to be capable of moving in an axial direction of the longitudinal axis member.

According to a fourth aspect of the present invention, in the medical device according to the third aspect, the closing member may be formed of an elastically deformable material, be introduced into the body in a state in which a diameter thereof is reduced less than that of an initial shape, and be restored to the initial shape in the body.

According to a fifth aspect of the present invention, the medical device according to the first aspect may further include an expansion part deformed between a first shape and a second shape enlarged over the first shape, and a manipulation member for changing the expansion part from the first shape to the second shape.

According to a sixth aspect of the present invention, a medical device for conducting negative pressure therapy on a local site in a body includes a longitudinal axis member has a lumen extending along a longitudinal axis so as to be capable of being inserted into the body; a suction member which is provided at a distal end of the longitudinal axis member so as to be capable of being inserted into a tubular cavity in the body, and the suction member having a contact surface for coming into close contact with an inner wall of the tubular cavity when inserted into the tubular cavity, and the suction member having a plurality of communication passages that are open to the contact surface and communicate with the lumen; a suction source which is provided at a proximal end of the longitudinal axis member so as to be connected to the lumen and the suction source suctioning the inner wall of the tubular cavity via the plurality of communication passages; and a closing member which is provided at an axial end of the suction member and the closing member airtightly sealing the inner wall that comes into close contact with the contact surface.

According to a seventh aspect of the present invention, the medical device according to the sixth aspect may further include an expansion part that is formed in an approximately cylindrical shape, is disposed inside the suction member, and enlarges dimensions of the suction member by changing from a first shape to a second shape.

According to an eighth aspect of the present invention, the medical device according to the seventh aspect may further include a covering member that is mounted on an outer or inner peripheral surface of the expansion part and holds airtightness of an inner cavity of the expansion part.

DETAILED DESCRIPTION OF THE INVENTION

Hereinafter, preferred embodiments of a medical device according to the present invention will be described with reference to the drawings.

Main targets of treatment in the present invention are cavities such as pustules and diverticula which are curved in a sac shape or in a form similar to a sac shape in addition to bursiform cavities such as the vermiform appendix of a body. Hereinafter, these are generically called "bursiform cavities". In addition to that, as described below, an anastomotic part of a digestive canal is also included among the treatment target sites. Further, in the present invention, "to treat inflammation" means that "negative pressure therapy" of applying negative pressure is conducted on a local region including the target site.

Further, in a first and a second embodiments described below, an example in which inflammation of a vermiform appendix, which is a bursiform cavity, known as appendicitis is treated by negative pressure therapy will be described.

Figure 1:
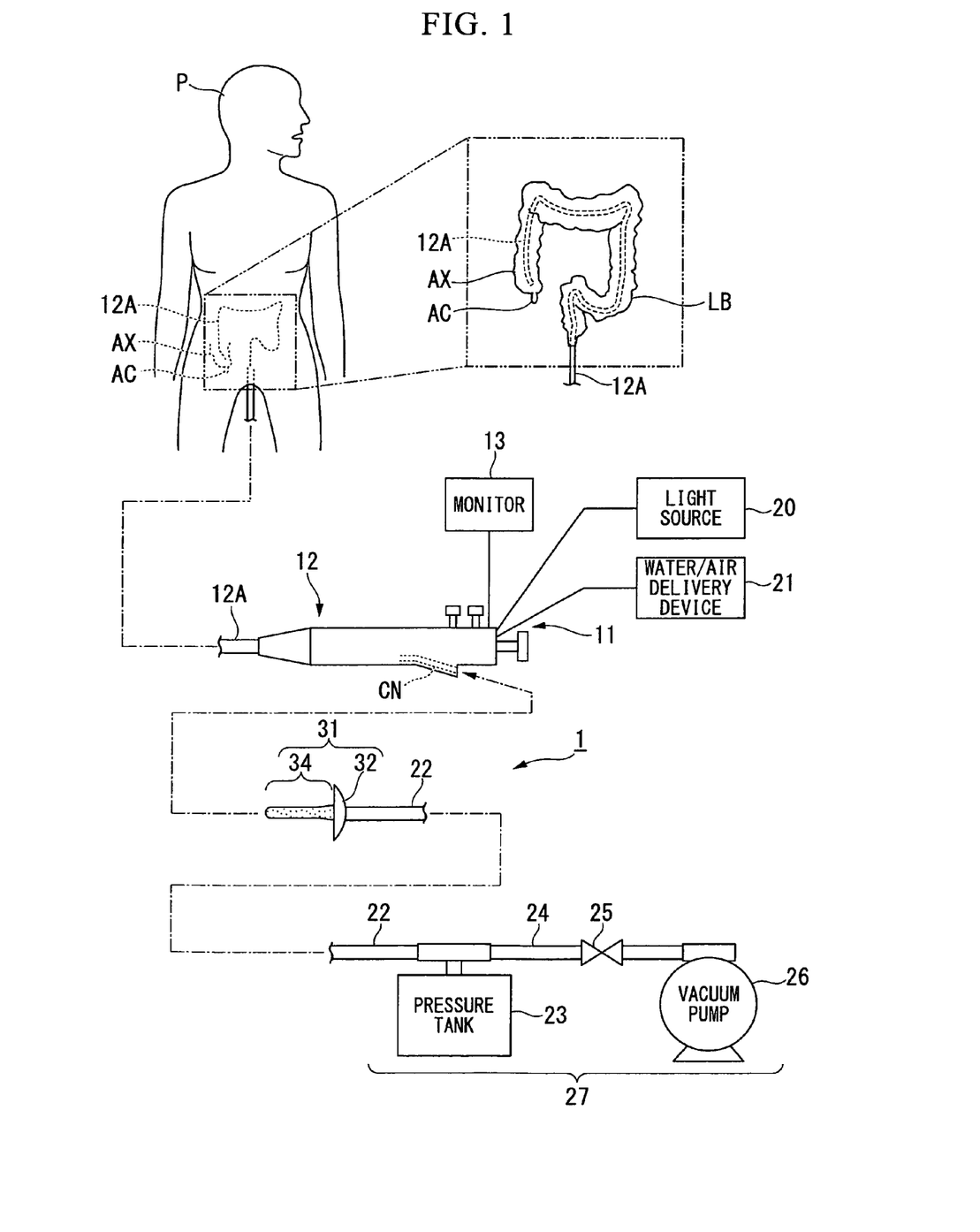
FIG. 1 is a configurational view for describing one example of a basic configuration of a medical treatment system for conducting negative pressure therapy according to a first embodiment.

One example of a basic configuration of a medical treatment system giving this medical treatment is shown in FIG. 1. A medical treatment system is a system that is equipped with the medical device according to the present embodiment and carries out a method of treating the inflammation of the bursiform cavity inside the body.

First Embodiment

As shown in FIG. 1, a medical treatment system 1 is equipped with an endoscopic device 11. The endoscopic device 11 is equipped with an endoscope 12 and a monitor 13. The endoscope 12 is a soft endoscope and has a flexible insertion part 12A that can be inserted into a body cavity LB in the body P. The endoscope 12 allows an image acquired by an image pickup device (not shown) provided at a distal end of the insertion part 12A to be displayed on the monitor 13. A variety of channels (hereinafter, collectively referred to merely as a "channel") CN for fulfilling various functions such as delivery of air, delivery of water, and insertion of a treatment tool required for examination and medical treatment using the endoscope are formed in the insertion part 12A along an axial direction of the insertion part 12A.

The medical treatment system 1 is equipped with a light source 20, a water/air delivery device 21, a suction catheter (longitudinal axis member) 22, and a suction source 27 in addition to the endoscopic device 11. The suction source 27 is equipped with a pressure tank 23, a tube 24, a valve (or a connector) 25, and a vacuum pump 26. Further, the medical treatment system 1 includes a medical treatment device (medical device) 31 held at the target site on which the negative pressure therapy is conducted.

The suction catheter 22 has a lumen (inner cavity) for suction. The suction catheter 22 is guided up to the vermiform appendix (bursiform cavity) AC in the body P via the channel CN of the insertion part 12A of the endoscope 12. The medical treatment device 31 is disposed at a distal end of the suction catheter 22, and the pressure tank 23 is connected to a proximal end of the suction catheter 22. The pressure tank 23 is connected to the vacuum pump 26 via the tube 24. The valve 25 interrupting a path of the tube 24 is interposed in the tube 24. For this reason, when the valve 25 is opened to drive the vacuum pump 26 for exhaustion of air, an interior of the pressure tank 23, i.e. an interior of the suction catheter 22, may be set to a desired value of negative pressure, and the negative pressure may be held.

The medical treatment device 31 is equipped with an applicator 34 and a closing member 32. The applicator 34 is inserted into the vermiform appendix AC. The closing member 32 is disposed at a proximal end side of the applicator 34 and has an approximate disc shape.

Figure 2A:
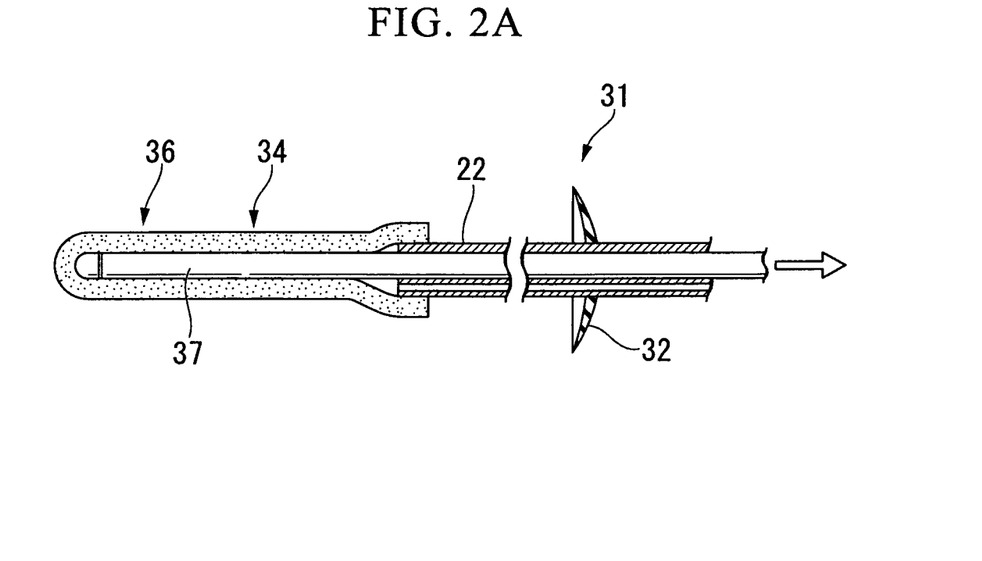
FIG. 2A illustrates a medical device according to the first embodiment.
Figure 2B:
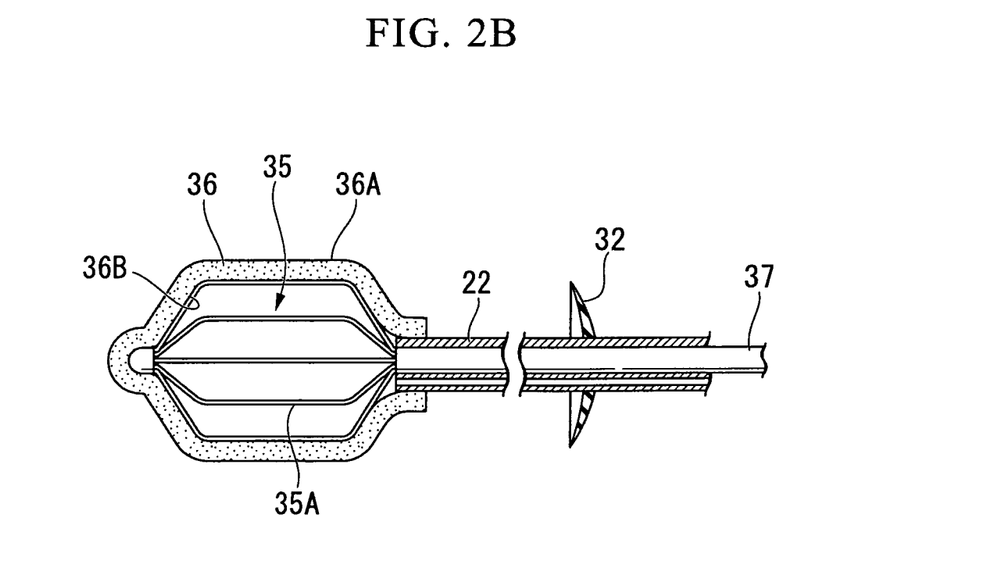
FIG. 2B illustrates the medical device according to the first embodiment.

FIG. 2A is a cross-sectional view showing the applicator 34 and the closing member 32 of the medical treatment device 31. FIG. 2B is a cross-sectional view showing a state in which the applicator 34 is enlarged. The applicator 34 is equipped with an expansion part 35 and a sponge (suction member) 36. The expansion part 35 is capable of being enlarged to a size so as to come into close contact with an inner surface of the bursiform cavity. The sponge 36 is disposed so as to cover an outer surface of the expansion part 35.

The expansion part 35 is formed by tying a distal end side of a plurality of wire rods 35A made of, for instance, a superelastic wire or a piano wire, and is disposed inside the sponge 36. A proximal end side of the expansion part 35 is fixed to the distal end of the suction catheter 22. In a natural state in which no external force is applied, as shown in FIG. 2B, the expansion part 35 is expanded in a shape (second shape) similar to a known basket shape used to collect and crush a biliary calculus. Each wire rod 35A of the expansion part 35 is deformed in an approximately linear shape (first shape) when introduced into the body and is stored in a storage sheath (manipulation member) 37 as shown in FIG. 2A. A proximal end of the storage sheath 37 protrudes from the proximal end of the suction catheter 22. When an operator pulls the proximal end of the storage sheath 37 to retreat the storage sheath 37 relative to the suction catheter 22, the expansion part 35 is enlarged in a basket shape as shown in FIG. 2B.

The sponge 36 is a porous soft member that has a known configuration with a plurality of vacancies and has a plurality of holes opening in an outer surface thereof. Since the vacancies formed in the sponge 36 partly communicate with one another, a plurality of communication passages (not shown) are present between the outer surface 36A and an inner surface 36B that is in contact with the expansion part 35. These communication passages communicate with the lumen of the suction catheter 22. Since the sponge 36 is soft, it enlarges in accordance with the shape of the expansion part when the expansion part 35 enlarges in the basket shape.

When the negative pressure from the pressure tank 23 is applied to the suction catheter 22, i.e. when air is suctioned, the suctioned air flows into the applicator from an exterior of the applicator 34 via the communication passages formed in the sponge 36. Further, the suctioned air reaches the pressure tank 23 from the applicator 34 through the lumen of the suction catheter 22. Thereby, the suction using the sponge 36 as a medium is conducted.

Figure 2C:
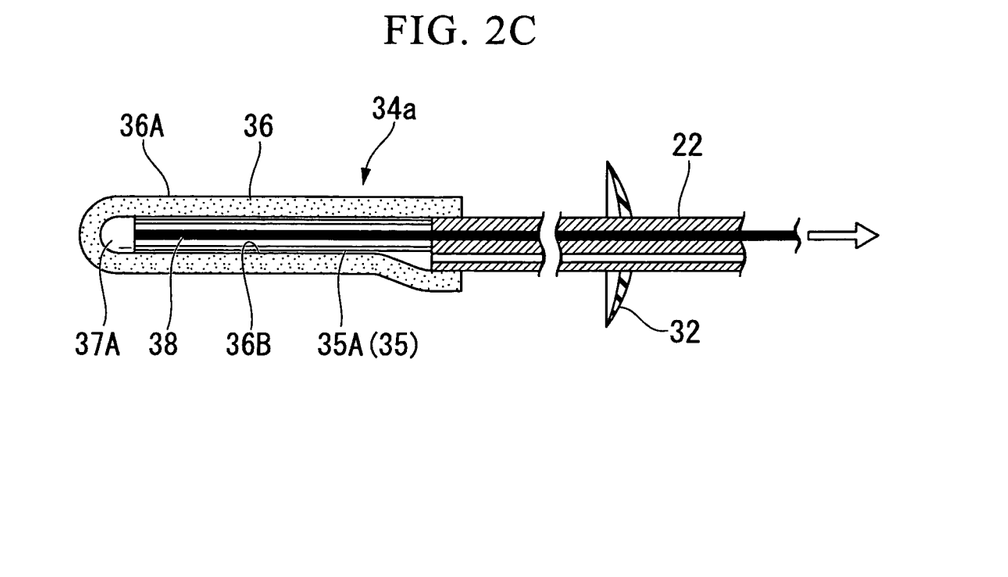
FIG. 2C illustrates another example of the medical device.
Figure 2D:
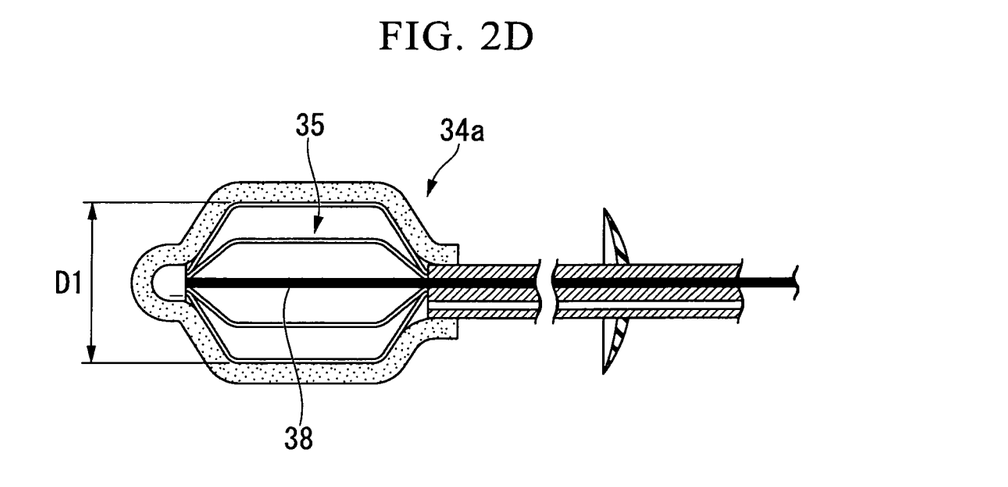
FIG. 2D illustrates another example of the medical device.

Another configuration example of the applicator 34 is shown in FIGS. 2C and 2D. This applicator 34a does not have the storage sheath 37. Alternatively, a manipulation wire (manipulation member) 38 is connected to a tip 37A that ties a distal end side of wire rods 35A of the expansion part 35. The manipulation wire 38 has such rigidity as not to be buckled even when the manipulation wire 38 is manipulated to be advanced toward the tip 37A. A proximal end of the manipulation wire 38 protrudes from the proximal end side of the suction catheter 22. When the applicator 34a is introduced into the body, an operator advances the manipulation wire 38 to deform the expansion part 35 in an approximately linear shape as shown in FIG. 2C. When the operator retracts the manipulation wire 38 in a state in which the applicator 34a comes out of the insertion part 12A, the expansion part 35 is enlarged in a basket shape as shown in FIG. 2D.

A positional relation between the manipulation wire 38 and the suction catheter 22 is fixed by, for instance, fixing the proximal end of the manipulation wire 38 to the suction catheter 22. Thereby, the applicator 34a can adjust a shape of the expansion part 35, particularly a radial dimension (dimension D1 shown in FIG. 2D), to a desired value. Therefore, as described below, a shape of the applicator can be adjusted to a process of treating the target site.

The closing member 32 is, for instance, an approximately disc-shaped member made of hole-free silicone having flexibility and may be elastically deformed. The closing member 32 is mounted on the suction catheter 22 so as to be able to move in a longitudinal axis direction of the suction catheter 22 and is allowed to move toward and away from the applicator 34.

An initial shape of the closing member 32 is preferably a shape curved so as to be recessed toward the distal end of the applicator 34. This is why the closing member 32 comes into close contact with an edge of the opening of the vermiform appendix AC. For this reason, the diameter of the closing member 32 must be large enough to block such an opening, and such a size can preferably be selected depending on a patient. Here, the sizes of the vermiform appendix AC and the closing member 32 will be taken by way of example as follows.

The vermiform appendix AC: Length from the opening to the distal end: about 50 to 100 mm, and inner diameter: about 5 to 10 mm; and The closing member 32: Material: silicone, diameter: about 20 to 30 mm, and thickness: about 1 to 3 mm.

Here, the body cavity LB indicates an entire site that ranges from the anus to the cecum AX of the colon. The colon LB extends from the anus through the rectum, the sigmoid colon, the descending colon, the transverse colon, and the ascending colon to the cecum AX. The vermiform appendix AC given as an example of the bursiform cavity is, as shown in FIG. 1, a small finger-shaped cul-de-sac protruding from a rear inner wall of a lower end of the cecum AX.

Figure 3:
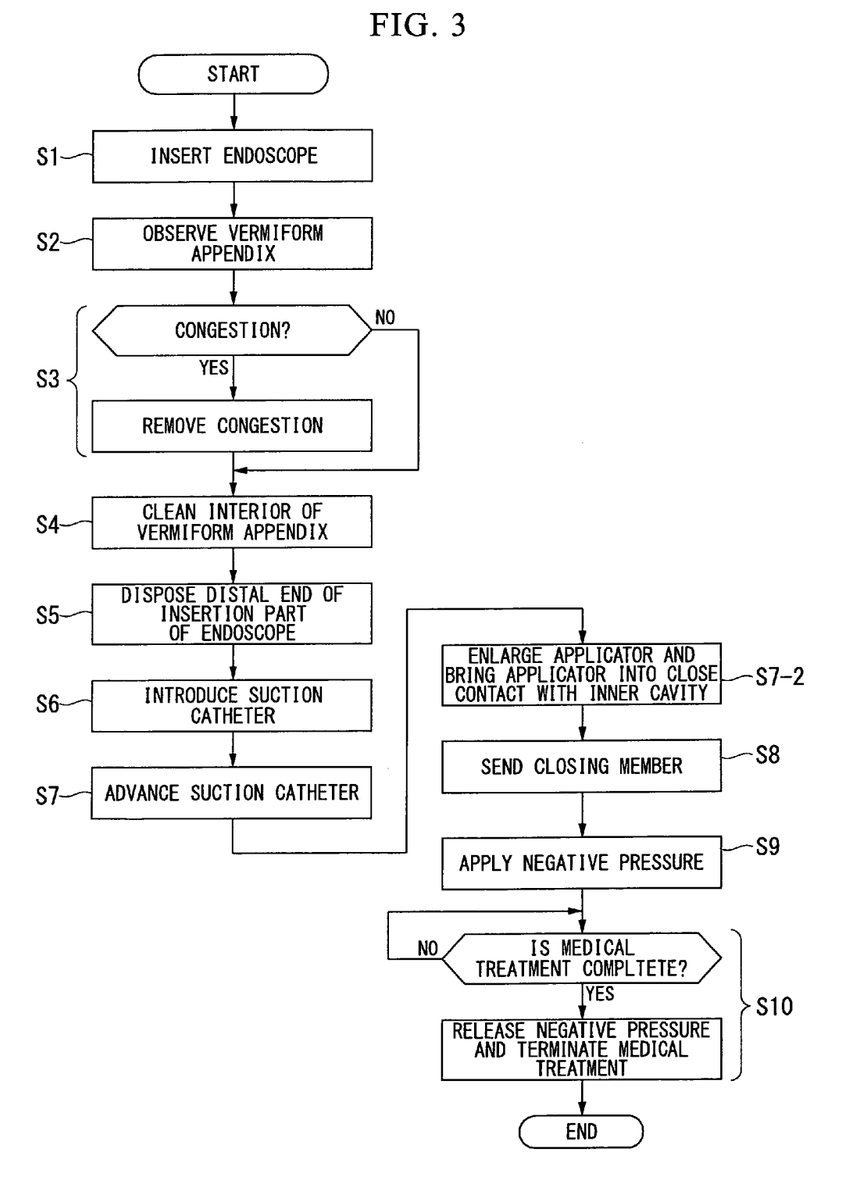
FIG. 3 is a flow chart for describing one example of a sequence of the negative pressure therapy conducted by the medical treatment system according to the first embodiment.

Next, a procedure of the negative pressure therapy using the medical treatment system 1 according to the present embodiment will be described with reference to FIGS. 3 and 4. FIG. 3 is a flow chart showing a flow of the procedure of the negative pressure therapy using the medical treatment system 1.

An operator inserts the insertion part 12A of the endoscope 12 from the anus of a body P to the vermiform appendix AC of the cecum AX via the colon LB (FIG. 3, step S1).

Next, the operator observes an interior and surroundings of an opening of the vermiform appendix AC using the endoscope 12 (step S2). As a result of the observation, if there is a cause of congestion of the vermiform appendix AC such as intestinal calculus, the cause is removed by using a treatment tool (not shown) introduced via the channel CN (step S3). Further, the water/air delivery device 21 is driven to clean the interior of the vermiform appendix AC (step S4).

Figure 4A:
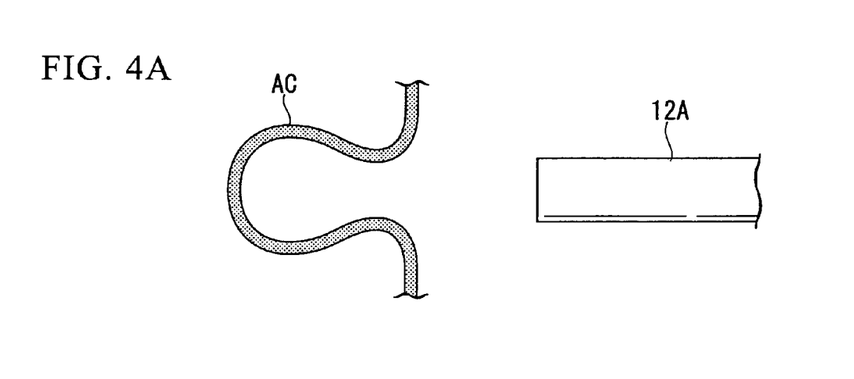
FIG. 4A describes an operation of the medical treatment system when used according to the first embodiment.
Figure 4B:
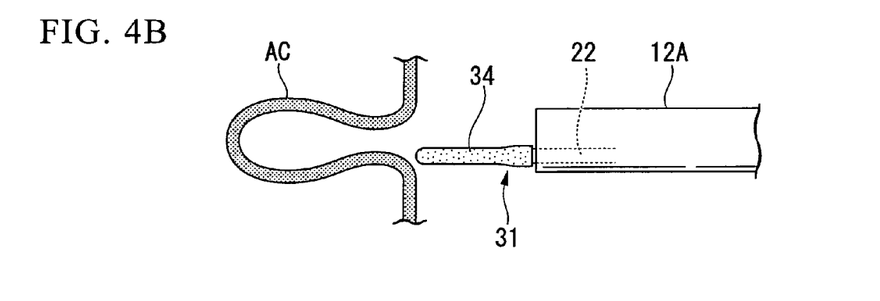
FIG. 4B describes an operation of the medical treatment system when used according to the first embodiment.
Figure 4C:
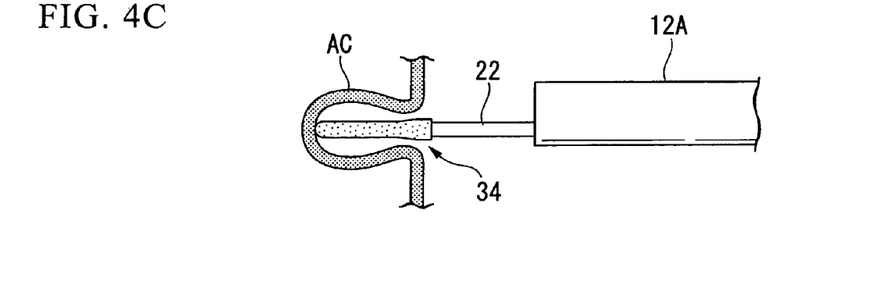
FIG. 4C describes an operation of the medical treatment system when used according to the first embodiment.
Figure 4D:
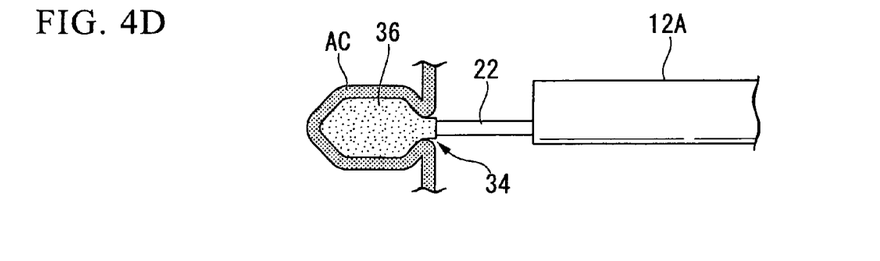
FIG. 4D describes an operation of the medical treatment system when used according to the first embodiment.
Figure 4E:
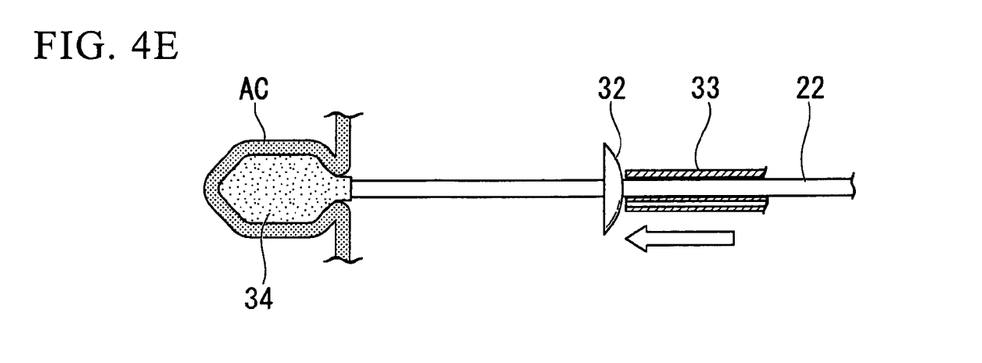
FIG. 4E describes an operation of the medical treatment system when used according to the first embodiment.
Figure 4F:
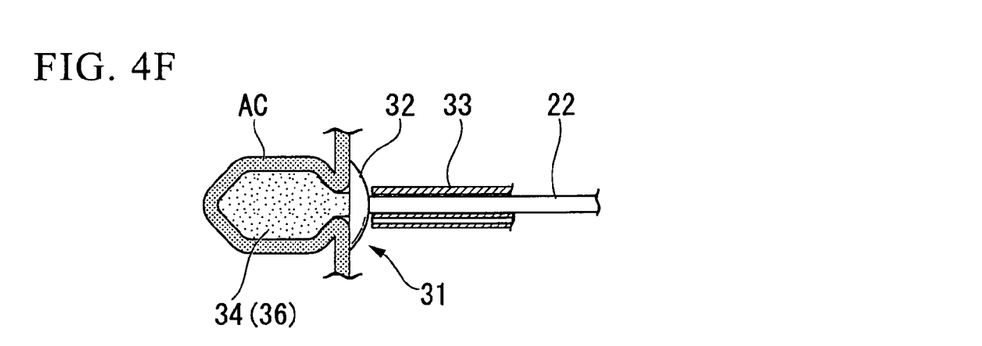
FIG. 4F describes an operation of the medical treatment system when used according to the first embodiment.

Subsequently, the operator disposes the distal end of the insertion part 12A of the endoscope 12 in front of the opening of the vermiform appendix AC (step S5, see FIG. 4A). Next, the operator inserts the suction catheter 22 into the channel CN of the insertion part 12A and introduces the suction catheter 22 into the body of the patient P. Further, the operator causes the applicator 34 of the medical treatment device 31 mounted on the distal end of the suction catheter 22 to protrude from the distal end of the insertion part 12A (step S6, see FIG. 4B). Thereby, the applicator 34 is positioned so as to face the opening of the vermiform appendix AC.

After the applicator 34 is positioned, the operator slowly advances the suction catheter 22 straight toward the opening of the vermiform appendix AC, and brings the distal end of the suction catheter 22 into contact with the bottom (wall of a depth direction) of the vermiform appendix AC (step S7). Thereby, the applicator 34 mounted on the distal end of the suction catheter 22 is also advanced slowly, penetrates into the vermiform appendix AC, and comes into contact with the bottom of the vermiform appendix AC (see FIG. 4C).

Then, the operator retracts the storage sheath 37 to enlarge the expansion part 35. Thereby, the applicator 34 is enlarged, and the outer surface (contact surface) 36A of the sponge 36 comes into close contact with the inner wall of the vermiform appendix AC (step S7-2, see FIG. 4D). As will be described below, when the applicator 34 has a different structure, this step may not be performed.

Subsequently, the operator leaves the applicator 34 and the suction catheter 22 and withdraws the endoscope 12 temporarily. Afterwards, the operator inserts the endoscope 12 into the body along the suction catheter 22 again, and advances the applicator 34 to an observable position. Then, the operator inserts the proximal end side of the suction catheter 22 into the closing member 32 and sends the closing member 32 toward the applicator 34 along the suction catheter 22 (step S8). For instance, when the closing member 32 is sent in by using a pusher tube (pusher) 33, the closing member 32 is advanced until it comes into contact with the periphery of the opening of the vermiform appendix AC (see FIGS. 4E and 4F). Thereby, the applicator 34 and the closing member 32 of the medical treatment device 31 are installed in the vermiform appendix AC. Here, a portion of the proximal end side of the suction catheter 22 comes out of the body from the anus of the patient P, and the suction catheter 22 is connected to the pressure tank 23.

Next, the operator drives the vacuum pump 26 to hold the pressure tank 23 at a desired value of negative pressure (step S9). As a result, the negative pressure is applied to the inner cavity of the vermiform appendix AC via the sponge 36 and the suction catheter 22. If it is confirmed that the negative pressure is applied, the endoscope 12 is withdrawn.

Figure 4G:
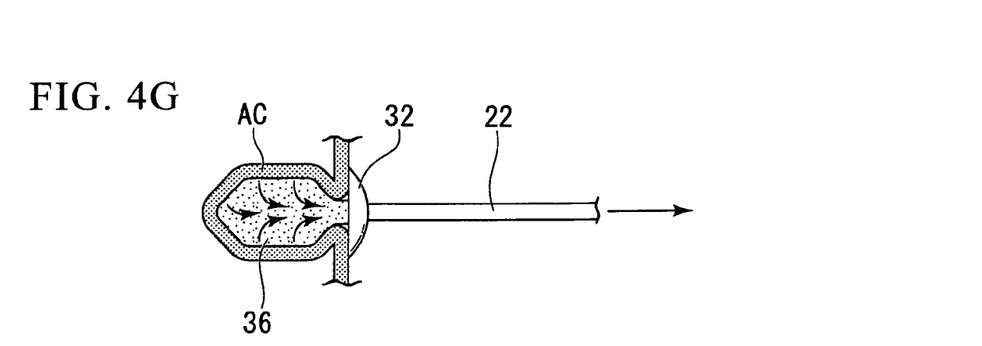
FIG. 4G describes an operation of the medical treatment system when used according to the first embodiment.

As the negative pressure is applied, as shown in FIG. 4G, the closing member 32 comes into close contact with the periphery of the opening of the vermiform appendix AC, and a pressure difference between the inner cavity of the vermiform appendix AC and the exterior of the vermiform appendix AC is positively maintained. That is, the pressure of the interior of the vermiform appendix AC is maintained at a desired value of negative pressure, but no negative pressure is applied to the interior of the cecum AX or the colon LB. The negative pressure state in which the suction catheter 22 comes out of the body is maintained for a predetermined period such as several hours or several days, and thereby the negative pressure therapy for the patient P is continuously conducted. The inner face of the vermiform appendix AC is suctioned via the closely contacted sponge 36 by the negative pressure therapy. Thus, blood circulation is improved, and cells are activated, so that inflammation is alleviated. Contents such as pus suctioned from the vermiform appendix AC by the negative pressure therapy are collected in the pressure tank 23 that doubles as a drainage collecting container. With the medical treatment of the inflammation, the cavity of the vermiform appendix AC may be reduced. However, since the wire rods 35A have elasticity, movement of the wall of the vermiform appendix associated with this reduction is not easily inhibited by the expansion part, and the expansion part 35 is also reduced with the reduction of the cavity of the vermiform appendix AC.

When the negative pressure therapy is completed, the operation of the vacuum pump 26 is stopped to return the pressure of the pressure tank 23 back to atmospheric pressure (step S10). Afterwards, the suction catheter 22 and the medical treatment device 31 are withdrawn to complete the medical treatment.

As described above, according to the negative pressure therapy using the medical treatment system 1 including the medical treatment device 31 of the present embodiment, the medical treatment device 31 equipped with the applicator 34 mounted on the distal end of the suction catheter 22 and the closing member 32 can be easily introduced up to the vermiform appendix AC under the observation of the endoscope. That is, the suction catheter 22 introduced into the body of the patient via the endoscope 12 is advanced, and thereby the applicator 34 can be easily inserted into and held in the vermiform appendix AC. Then, the sent closing member 32 comes into contact with the edge of the opening of the vermiform appendix AC, and then the negative pressure is applied via the suction catheter 22. Thereby, the closing member 32 comes into close contact with the opening of the vermiform appendix AC, and the interior of the vermiform appendix AC is adequately sealed. For this reason, only the internal space of the vermiform appendix AC can be locally formed in a negative pressure state, and the negative pressure state can be maintained in an easy and proper way. Thereby, the negative pressure therapy can be simply and reliably conducted on the vermiform appendix AC. Further, since a region to which the negative pressure is applied is small, the negative pressure can be more efficiently applied.

Further, since the applicator 34 has the expansion part 35, even when the target bursiform cavity is enlarged by inflammation, a surface area is increased up to the same degree as an internal area of the corresponding cavity, and the suction member such as the sponge can adequately come into close contact with the inner face of the cavity.

Furthermore, since the wire rods 35A have elasticity, they are enlarged so as to follow the inner face of the vermiform appendix AC when enlarged, and an excessive load is not applied to the wall of the vermiform appendix AC.

On the other hand, the surface area of the applicator does not essentially need to be increased to be the same as the internal area of the cavity. In a state before the negative pressure is applied, a slight gap may remain between the suction member and the inner surface of the cavity. Even in this case, when sealed by the closing member 32 so as to apply the negative pressure, the inner cavity of the cavity is reduced, and the suction member and the inner face of the cavity come into close contact with each other. The negative pressure therapy is adequately conducted. However, when the surface area of the applicator is too small with respect to the internal area of the cavity, a part of the inner cavity of the cavity is folded when the inner cavity of the cavity is reduced, and a part of the inner surface does not come into contact with the suction member. Furthermore, to improve the suction mediating the communication passages of the suction member, it is more preferable to prevent a fluid channel having low suction resistance from being formed between the folded sites. Accordingly, the applicator preferably has the expansion part. Without the expansion part, a plurality of sizes of suction members are preferably provided and allowed to be selected according to the internal area of the cavity.

In the present embodiment, the example in which the closing member 32 is moved using the pusher tube 33 has been described, neither the structure nor the constitution of the pusher is limited thereto. If the pusher can be advanced or retracted along the longitudinal axis member and move the closing member, the configuration thereof is not particularly limited to a specific structure of the pusher.

Further, in the present embodiment, the example in which the medical treatment device and the suction catheter are introduced via the channel formed in the endoscope has been described. However, in place of this, as in a second embodiment to be described below, the medical treatment device and the suction catheter may be introduced via an external channel mounted on the insertion part of the endoscope.

(Modification)

The applicator and the closing member used in the aforementioned embodiment are not limited to the aforementioned configurations, but may be deformed in various forms.

Figure 5A:
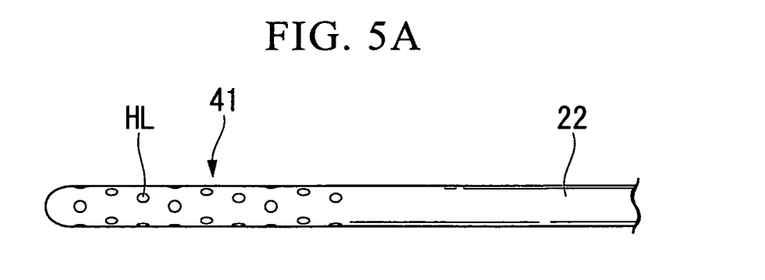
FIG. 5A illustrates a modification of an applicator.

A modification of the applicator according to the present embodiment is shown in FIG. 5A. This applicator 41 has flexibility and a hollow interior and is integrally connected to the suction catheter 22. Further, the applicator 41 is formed with a plurality of holes (communication passages) HL penetrating between the interior and exterior thereof, and a portion where the holes HL are formed becomes a suction member.

Figure 5B:
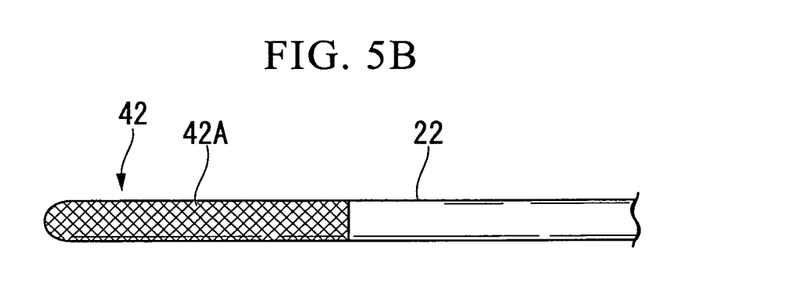
FIG. 5B illustrates a modification of the applicator.

Another modification of the applicator according to the present embodiment is shown in FIG. 5B. The applicator 42 according to this modification is a mesh-shaped or porous member made of, for instance, a fluorine-based resin or a resin such as nylon, and is equipped with a suction member 42A having a plurality of communication passages that are open to an outer face thereof and communicate with an interior thereof. This applicator 42 has a similar shape to the aforementioned applicator 41 and is integrally formed at the distal end of the suction catheter 22.

The applicators 41 and 42 according to the present embodiment have the same diameter as the suction catheter 22 without the expansion part. However, the applicators 41 and 42 may be enlarged in diameter so that a surface area of the outer surface of the suction member is identical to that of the inner wall of the target site such as the vermiform appendix AC. In this case, the suction member may be formed of a material that can be deformed to such a degree as to pass through the interior of the channel CN.

Figure 5C:
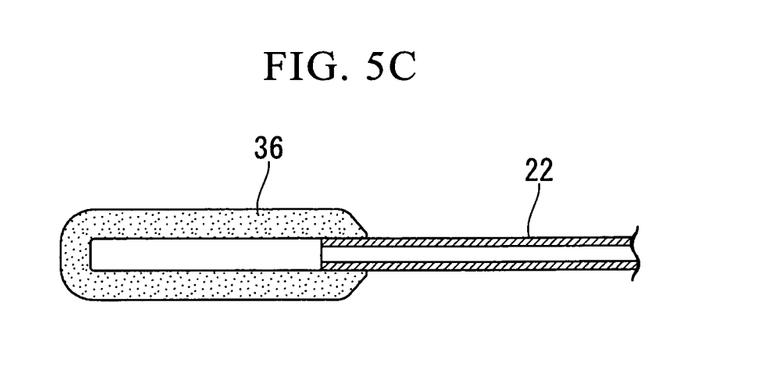
FIG. 5C illustrates a modification of the applicator.

Further, as shown in FIG. 5C, a configuration in which only a typical sponge 36 is mounted as the suction member on the distal end of the suction catheter 22 may be used as the applicator. Even in this case, the opening of the target site is sealed by the closing member, and thereby the negative pressure therapy can be adequately conducted.

Figure 6A:
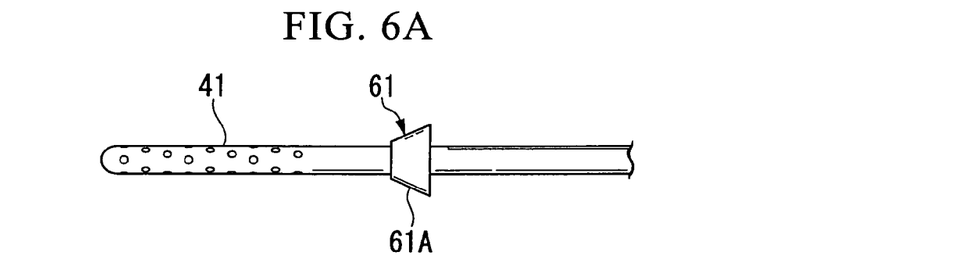
FIG. 6A illustrates a modification of a closing member.
Figure 6B:
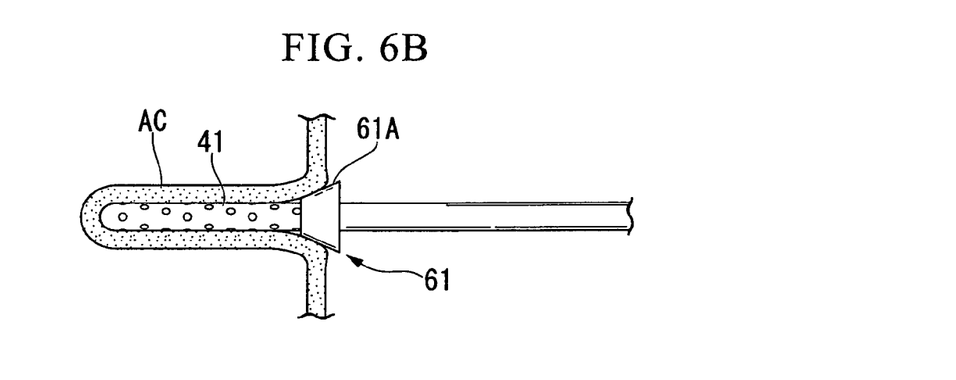
FIG. 6B illustrates a modification of the closing member.

A modification of the closing member is shown in FIG. 6A. This closing member 61 may be properly used in combination with the applicator 41 or 42 of the aforementioned modification. The closing member 61 has a taper 61A formed so as to be nearly matched with a shape of an inlet of the opening of the vermiform appendix AC. Therefore, as the taper 61A comes into close contact with the opening, the vermiform appendix AC can be sealed so as to provide a plug for the opening, and a position of the closing member 61 can be prevented from being offset for a standby time required to apply the negative pressure. Further, as the negative pressure is applied, as shown in FIG. 6B, a capability to come into contact with the opening is further increased, and the negative pressure therapy can be adequately conducted.

Figure 6C:
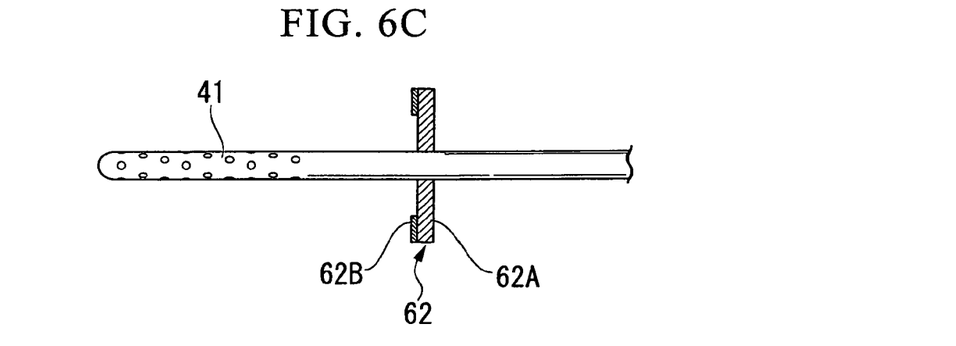
FIG. 6C illustrates another modification of the closing member.
Figure 6D:
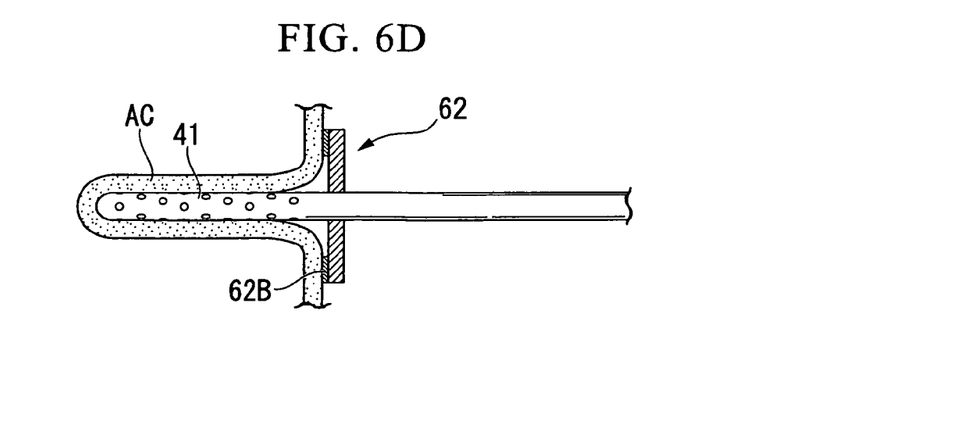
FIG. 6D illustrates another modification of the closing member.

Another modification of the closing member is shown in FIG. 6C. This closing member 62 may also be properly used in combination with the applicator 41 or 42 of the modification. This closing member 62 has a disc 62A and an adhesive layer 62B. The disc 62A is formed of a resin such as silicone. The adhesive layer 62B is formed in a ring shape along a peripheral edge of a face of the disc 62A which is located at the side of the vermiform appendix. When the closing member 62 is used, the adhesive layer 62B is adhered to the edge of the opening of the vermiform appendix AC as shown in FIG. 6D, and the opening can be adequately sealed. Further, position aberration of the closing member 62 before the negative pressure is applied can be prevented by the adhesive layer 62B. In this modification, the adhesive layer 62B may not be essentially formed in the ring shape. The adhesive layer 62B may have a closed shape that can surround the opening.

Second Embodiment

A second embodiment of the medical treatment system according to the present invention will be described with reference to FIGS. 7A to 7C. In the present embodiment and the following embodiment, constitutional members having an operation equal or equivalent to that of the aforementioned first embodiment are given the same symbols, and description thereof will be omitted or simplified.

Figure 7A:
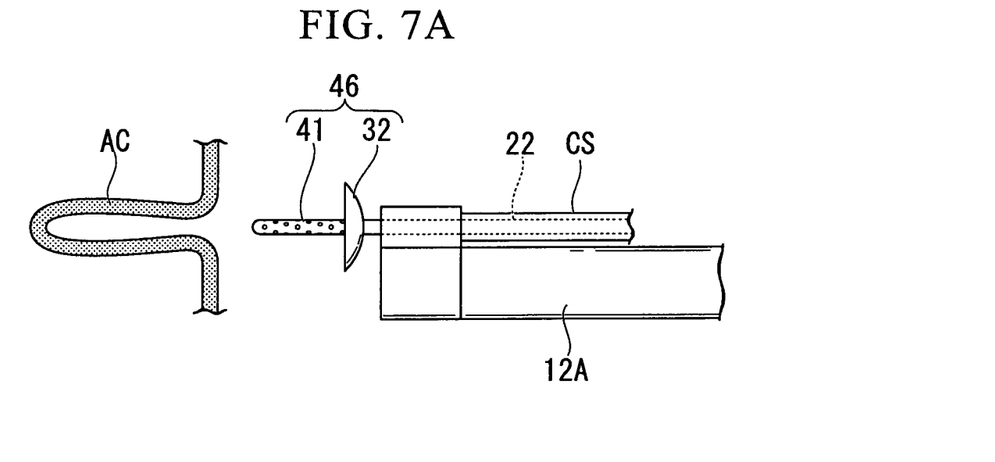
FIG. 7A describes a medical device when used according to a second embodiment and an operation of the medical device.
Figure 7B:
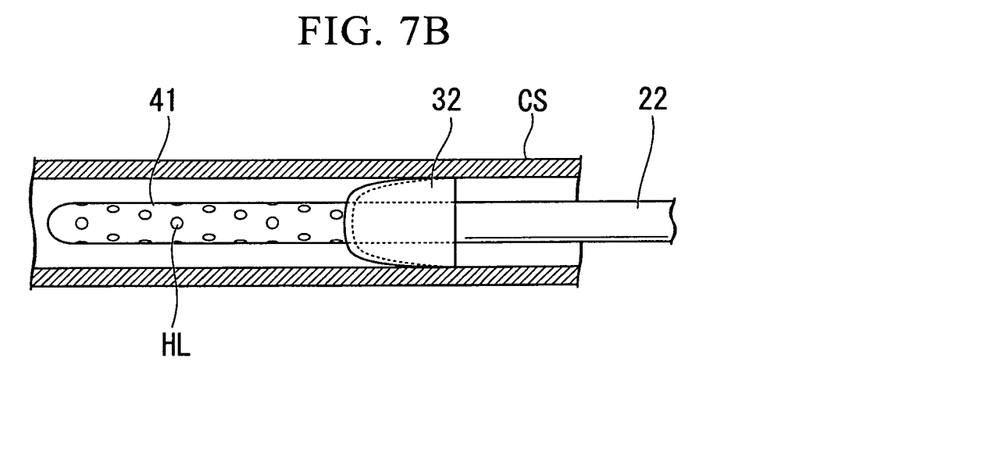
FIG. 7B describes the medical device when used according to the second embodiment and the operation of the medical device.
Figure 7C:
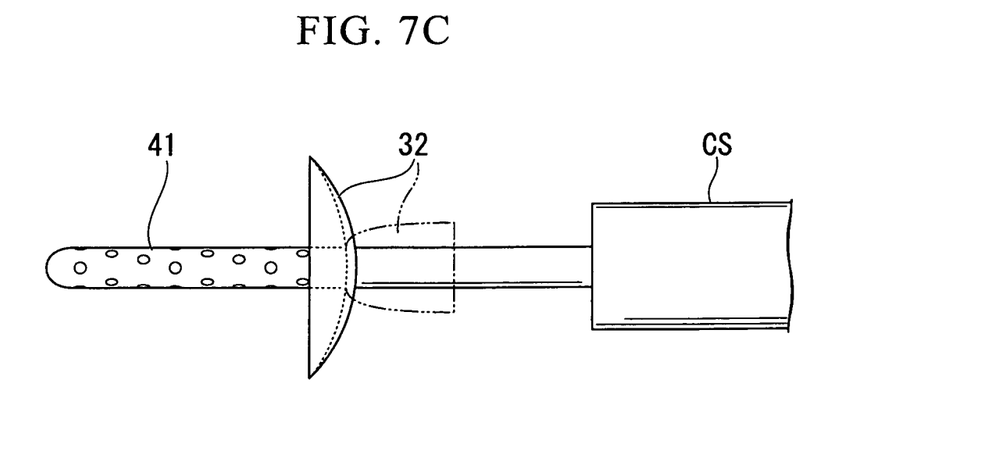
FIG. 7C describes the medical device when used according to the second embodiment and the operation of the medical device.

A medical treatment device 46 using this medical treatment system is shown in FIG. 7A. The medical treatment device 46 has a structure in which a closing member 32 is integrally mounted on an applicator 41 located at a distal end of a suction catheter 22 from the first. That is, the closing member 32 does not move along the suction catheter 22. Configurations such as a material and a shape of the closing member 32 are equivalent to those of the first embodiment. Structures of the suction catheter 22 and the applicator 41 are equivalent to those of the first embodiment. The integrated applicator 41 (the applicator 41 integrally connected to the suction catheter 22) and closing member 32 are inserted into an external guide tube CS of the endoscope 12 as shown in FIG. 7B. The closing member 32 is folded in the guide tube CS toward a proximal end side of the suction catheter 22 by elastic deformation. For this reason, when the suction catheter 22 is advanced to protrude from a distal end of the guide tube CS, the closing member 32 is released from the folded state by its elastic force as shown in FIG. 7C and returns to an initial shape that can close the vermiform appendix AC.

Since the closing member 32 is fixed adjacent to a proximal end of the applicator 41, when the applicator 41 is inserted into the vermiform appendix AC under the observation of the endoscope, the integrated closing member 32 comes into contact with the opening of the vermiform appendix AC so as to close the opening as in the first embodiment. As a result, as in the first embodiment, the vermiform appendix AC can be sealed, and the negative pressure therapy can be adequately conducted.

Therefore, effects similar to those of the first embodiment can also be exerted by the medical treatment device 46 according to the second embodiment. Further, in the case of the medical treatment device 46, since an axial position of the closing member 32 relative to the applicator 41 is predetermined, trouble of sending the closing member can be saved, compared to the case in which the closing member is sent behind as in the first embodiment.

According to an individual difference of patients, the vermiform appendix AC has a different size. For this reason, various types of medical treatment devices are preferably prepared in which sizes of the applicator and the closing member and a fixed position of the closing member 32 relative to the applicator are changed in advance. In detail, the medical treatment device may be selected in accordance with the size of the vermiform appendix AC confirmed by the observation of the endoscope in advance.

Further, the medical treatment device of the present embodiment may be inserted into the channel CN rather than into the external guide tube CS. Further, the medical treatment device may be attached to the guide mounted on the insertion part 12A and be introduced into the body in parallel to the insertion part 12A without being inserted into the guide tube.

Further, in the present embodiment, the example in which the covering material is mounted on the outer peripheral side of the expansion part has been described. However, the covering material may be mounted on an inner peripheral side of the expansion part.

Third Embodiment

The present embodiment has a configuration that can be properly used in a case in which the target on which the negative pressure therapy is conducted is not the bursiform cavity.

Figure 8A:
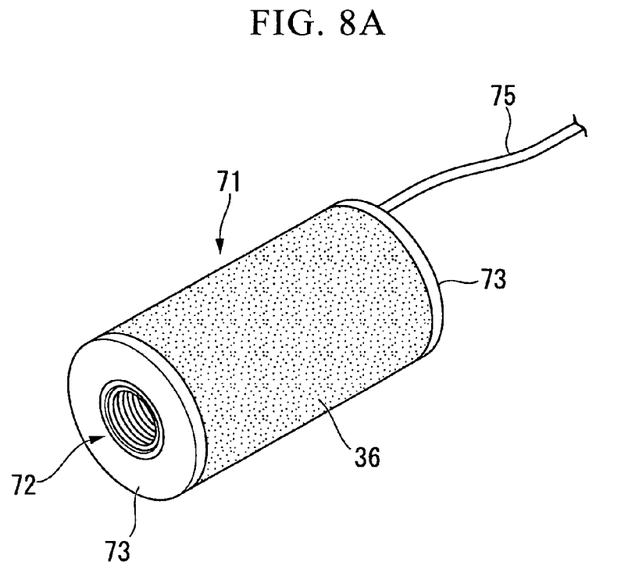
FIG. 8A is a perspective view showing a medical device in a third embodiment.
Figure 8B:
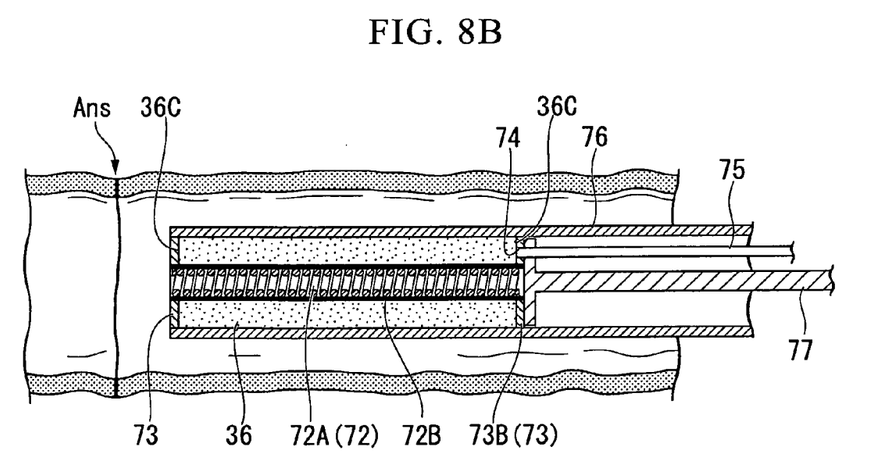
FIG. 8B illustrates an operation of the medical device when used.
Figure 8C:
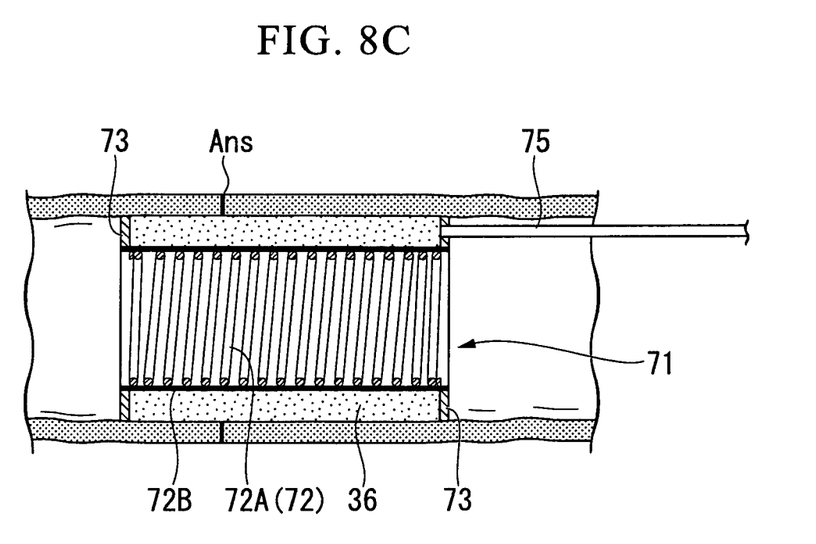
FIG. 8C illustrates an operation of the medical device when used.

FIG. 8A is a perspective view showing a medical treatment device 71 according to the present embodiment. FIGS. 8B and 8C are views showing an operation of the medical treatment device 71 when used. As shown in FIGS. 8A and 8B, the medical treatment device 71 is equipped with an expansion part 72, a sponge 36, and closing members 73. The sponge 36 is mounted so as to cover an outer circumferential surface of the expansion part. The closing members 73 are mounted on opposite axial ends of the expansion part.

The expansion part 72 is formed of a wire rod 72A in an approximately cylindrical shape and is enlarged to a predetermined diameter in a natural state. A covering material 78 having airtightness is mounted on the outer circumferential surface of the expansion part 72, and airtightness is secured between the outer circumferential surface and an inner cavity. As this expansion part 72 and covering material 78, for instance, a known covered stent or a member having a structure similar to that of the covered stent may be used. In FIGS. 8A and 8C, the expansion part formed of a coil-shaped wire rod 72A is shown as an example. However, in addition to this, a wire mesh-shaped structure may be used as the expansion part.

The closing members 73 are formed in an approximate doughnut shape, in the center of which an opening is formed, and each is formed of a material such as silicone having airtightness and flexibility. The closing members 73 are mounted on the opposite axial ends of the expansion part 72 and airtightly cover opposite axial end faces 36C of the sponge 36 disposed in the approximately cylindrical shape. Further, inner circumferences of the openings of the centers of the closing members 73 are connected with the covering material 78 so as to retain the airtightness. Of the two closing members, the closing member 73B of the proximal end side is provided with a through-hole 74 penetrating in a thickness direction, and a tube (longitudinal axial member) 75 for applying negative pressure is connected to the through-hole 74. Thereby, a lumen of the tube 75 communicates with communication passages of the sponge 36 and is connected to a pressure tank 23 and a vacuum pump 26 same as the suction catheter 22. An inner cavity of the approximately cylindrical expansion part 72 is configured so that the airtightness thereof is secured by the covering material 78 and that opposite ends thereof are open.

an operation when the medical treatment device 71 according to the present embodiment configured as described above is used will be described. A main target site of the medical treatment device 71 is an anastomotic part Ans formed by excising a portion of a digestive canal (see FIG. 8B).

First, in a state in which the medical treatment device 71 is reduced in diameter (a state in which the expansion part 72 has a first shape), as shown in FIG. 8B, an operator stores the medical treatment device in a storage sheath 76 and introduces the medical treatment device to the vicinity of the anastomotic part Ans while observing the medical treatment device with the endoscope 12.

The operator positions the medical treatment device 71 so that the outer peripheral surface of the sponge 36 crosses proximal and distal sides of the anastomotic part Ans. The proximal end side of the medical treatment device is held by a rod 77 inserted into the storage sheath 76, and in the meantime the storage sheath 76 is retracted relative to the rod 77. Then, the medical treatment device 71 moves out of the storage sheath 76, and the expansion part 72 is enlarged to a predetermined diameter (second shape). As shown in FIG. 8C, the outer peripheral surface (contact face) 36A of the sponge 36 comes into close contact with a wall of the digestive canal. After the expansion part 72 is enlarged, the storage sheath 76 and the rod 77 may be withdrawn.

Here, as the closing members 73 come into close contact with the wall of the digestive canal in a peripheral direction, the space in which the sponge 36 is located is sealed by retaining airtightness with the aid of the two closing members 73, the covering material 78 mounted on the expansion part 72, and the wall of the digestive canal. In this state, as the negative pressure is applied to the space in which the sponge 36 is located by the tube 75, the negative pressure therapy can be adequately conducted on a local region including the anastomotic part Ans.

According to the medical treatment device 71 according to the present embodiment, even when a site other than the bursiform cavity, such as the anastomotic part Ans, is the target site, the local negative pressure therapy can be properly conducted without maintaining a wide range such as an entire interior of the digestive canal under negative pressure.

Further, the expansion part 72 is formed in an approximately cylindrical shape, and the closing members 73 have a shape in which the corresponding openings are not blocked. For this reason, the opposite ends of the inner cavity are open, and liquid and solid can pass through the inner cavity of the expansion part 72 even in the process of conducting the negative pressure therapy. Accordingly, the negative pressure therapy can be properly conducted on the anastomotic part without blocking a lumen tissue of the digestive canal.

Figure 9A:
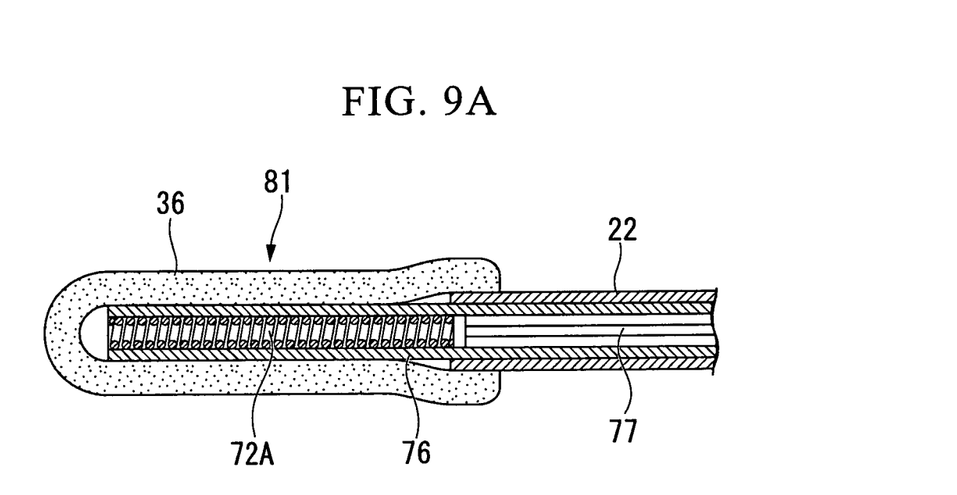
FIG. 9A illustrates a modification of the applicator.
Figure 9B:
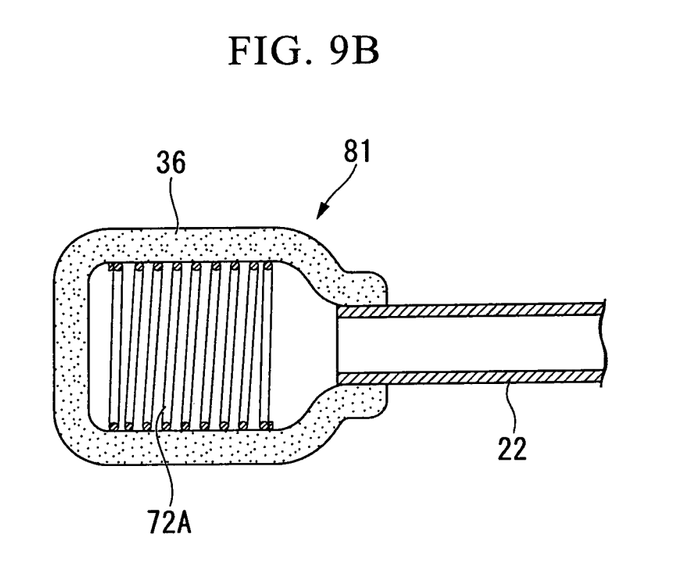
FIG. 9B illustrates another modification of the applicator.

As shown in FIGS. 9A and 9B, the structure such as the expansion part according to the present embodiment can be applied to an applicator 81 for the bursiform cavity. In this case, a covering material covering an outer surface of a wire rod 72A is not required, and only the wire rod 72A may be used as the expansion part. Further, the storage sheath 76 may be inserted into the suction catheter 22 so as to store only the wire rod 72A. The suction member such as the sponge 36 is preferably disposed so as to block an opening of a distal end side of the approximately cylindrical expansion part 72. When the wire rod 72A is enlarged, the storage sheath 76 may be retracted while the wire rod 72A is being held by the rod 77, roughly similar to the medical treatment device 71.

While embodiments and modifications of the invention have been described, it should be understood that the invention is not limited to the configurations set forth in the aforementioned embodiments and modifications. Accordingly, additions, omissions, substitutions, and other modifications of the configurations can be made without departing from the spirit or scope of the present invention, and the constitutions can also be carried out in appropriate combination with the well-known configurations. The invention is not limited by the above description, and is limited only by the scope of the appended claims.

What is claimed is:

1. A medical device for endoscopically conducting negative pressure therapy on a bursiform cavity having an opening in a body, the medical device comprising:
   a longitudinal axis member comprising a lumen extending from a proximal end to a distal end of the longitudinal axis member along a longitudinal axis and that is configured to be inserted through the bursiform cavity, the longitudinal axis member is configured to be inserted into the body;
   an expansion part which is provided at the distal end of the longitudinal axis member, the expansion part having a plurality of wire members being deformed outward in a radial direction of the longitudinal axis member to follow an inner wall of the bursiform cavity;
   a suction member comprising a porous sponge member including a plurality of vacancies and covers an outer surface of the expansion part, the suction member is configured to be inserted into the bursiform cavity in an axial direction of the longitudinal axis member from an opening of the bursiform cavity to a position where the suction member contacts with a bottom of the bursiform cavity to determine a position at which the expansion part is expanded, and when the suction member is inserted into the bursiform cavity and the expansion part is expanded, a region from the opening of the bursiform cavity to the inner wall of the bursiform cavity is closely contacted by a contact surface of the suction member and sucked by the suction member;
   a suction source which is provided at the proximal end of the longitudinal axis member and connected to the lumen to suck the inner wall of the bursiform cavity via the suction member; and
   a closing member which is provided at an axial end of the suction member to close the opening of the bursiform cavity to airtightly seal the bursiform cavity.

2. The medical device according to claim 1, wherein the closing member is curved toward the suction member in a concave shape.

3. The medical device according to claim 1, further comprising a pusher for moving the closing member, wherein
   the lumen is connected with the suction member, and
   the closing member is mounted on the longitudinal axis member.

4. The medical device according to claim 3, wherein the closing member is formed of an elastically deformable material, is introduced into the body in a state in which a diameter thereof is reduced less than that of an initial shape, and is restored to the initial shape in the body.

5. The medical device according to claim 1, further comprising:
   a manipulation member which is used to deform the expansion part between a first shape and a second shape enlarged over the first shape.

6. A medical device for conducting negative pressure therapy on a local site in a body, the medical device comprising:
   a longitudinal axis member which has a lumen extending from a proximal end to a distal end of the longitudinal axis member along a longitudinal axis and configured to be inserted into the body;
   an expansion part which is provided at the distal end of the longitudinal axis member, the expansion part having a wire member that is formed in a cylindrical shape with a predetermined length along the longitudinal axis and configured to be enlarged to a predetermined diameter;
   a suction member comprising a porous sponge member including a plurality of vacancies, covers an lateral surface of the expansion part and is provided at a distal end of the longitudinal axis member, and when the suction member is inserted into the tubular cavity and the expansion part is expanded, a predetermined region of the inner wall of the tubular cavity is closely contacted by a contact surface of the suction member and sucked by the suction member;
   a suction source which is provided at a proximal end of the longitudinal axis member and connected to the lumen, the suction source sucking the inner wall of the tubular cavity via the suction member; and
   a closing member which is provided at two axial ends of the suction member to airtightly seal the inner wall of the tubular cavity that is closely contacted by the contact surface of the suction member.

7. The medical device according to claim 6, wherein the expansion part that is formed in an approximately cylindrical shape, is disposed inside the suction member, and enlarges dimensions of the suction member by changing from a first shape to a second shape.

8. The medical device according to claim 7, further comprising a covering member that is mounted on an outer or inner peripheral surface of the expansion part and retains airtightness of an inner cavity of the expansion part.

9. The medical device according to claim 6, wherein the expansion part is expanded by a negative pressure from the suction member via a tube which is provided at the closing member provided at the distal end of the longitudinal axis member.

* * * * *